United States Patent [19]

McGough et al.

[11] Patent Number: 4,769,031
[45] Date of Patent: Sep. 6, 1988

[54] VENTRICULAR ACCESS DEVICE AND METHOD

[76] Inventors: Edwin C. McGough, 1327 E. Michigan Ave., Salt Lake City, Utah 84105; Mark M. Boucek, 4231 Emigration Canyon Rd., Salt Lake City, Utah 84108

[21] Appl. No.: 878,185

[22] Filed: Jun. 25, 1986

[51] Int. Cl.⁴ .............................................. A61F 2/06
[52] U.S. Cl. ..................................................... 623/1
[58] Field of Search ................. 623/1; 604/44, 51, 52, 604/264, 273, 175

[56] References Cited

U.S. PATENT DOCUMENTS 3,920,023 11/1975 Dye ......................................... 604/51
4,118,806 10/1978 Porier ....................................... 623/1

Primary Examiner—Richard J. Apley
Assistant Examiner—James Prizant
Attorney, Agent, or Firm—Jon C. Christiansen

[57] ABSTRACT

A ventricular access device and method. In accordance with the method a grommet is introduced into a ventricle and the grommet conduit is caused to penetrate the ventricle's myocardium in an inside to outside manner. The portion of the grommet conduit external to the ventricle is connected to a primary external conduit. The inventive device is a grommet in the form of a conduit and an extension (e.g. flange) extending outwardly from the conduit. The grommet conduit provides an outlet for the egress of blood from the ventricle. The extension provides contact against the inner wall of the ventricle to hold the grommet in place notwithstanding the outward flow of blood from the ventricle.

17 Claims, 2 Drawing Sheets

VENTRICULAR ACCESS DEVICE AND METHOD

INTRODUCTION

Our invention relates to a ventricular access device and method. The device and method provide a means and surgical procedure for the creation of an unobstructed outlet for blood flow from the ventricle of a heart.

To understand the invention, it is necessary to understand the human heart. The heart is located in the thoracic (chest) cavity above the diaphragm, behind the sternum (breastbone) and between the lungs. Septa partition the heart into a left half and a right half. Each half consists of an atrium and a ventricle. The atria are generally identified as the left atrium and the right atrium. The ventricles are generally identified as the left ventricle and the right ventricle. The left atrium is a chamber into which oxygenated blood from the lungs is pumped. Blood is pumped from the left atrium through an atrioventricular valve to the left ventricle chamber from which blood is further pumped to the descending aorta for systemic circulation. The right atrium is a chamber into which blood flows after systemic circulation. Blood is pumped from the right atrium through an atrioventricular valve to the right ventricle chamber from which blood is pumped to the pulmonary artery for pulmonary circulation. The wall of each ventricle is comprised of three layers of muscular tissue: the endocardium (inner layer), the myocardium (middle layer) and the epicardium (external layer). As used in this disclosure and the appended claims the term myocardium will mean (for the sake of economy of words) the endocardium, myocardium and epicardium collectively.

If the flow of blood from a ventricle is blocked or obstructed, it may be desirable or necessary to establish an unobstructed outlet for the flow of blood from the ventricle to the descending aorta or pulmonary artery. There are also certain congenital heart defects that require connecting the left ventricle to the pulmonary artery or the right ventricle to the descending aorta. An example of the latter is hypoplastic left heart syndrome (HLH). Furthermore, it may be desirable in certain cases to establish an outflow of ventricle blood which is directed to an artificial ventricle or other artificial heart assist device.

The prior art approach to the establishment of a ventricle outlet can be characterized as an "outside to inside" approach. In brief summary, the prior art procedure is as follows. A portion (typically of circular cross-section) of tissue is cored out of the ventricle's myocardium. From the outside of the ventricle a stint is positioned into the myocardium. The stint is essentially a conduit which provides an outlet for the flow of blood from the ventricle. To hold the stint in place, it is sutured to the myocardium (or more precisely the epicardium). The stint is connected to a primary conduit which is connected to the descending aorta or pulmonary artery.

The prior art procedure has significant disadvantages. The prior art procedure requires a cardiopulmonary bypass which places the life of the patient at risk and creates substantial additional financial cost. A portion of the ventricle's myocardium is removed and the sutures immobilize an additional area of myocardium. This damages the ventricle and interferes with the contraction and functioning of the ventricle.

The device and method of this invention provide a means and surgical procedure which obviate the need for cardiopulmonary bypass and the need to remove a myocardium core and to use immobilizing sutures. Thus, the invention has the advantages of substantially reducing the risk, cost and damage incurred in the establishment of an outlet for the flow of blood from a ventricle. These advantages and objects of the invention as well as other advantages and objects will be obvious to a person of ordinary skill in the relevant art upon a study of this disclosure and the appended claims.

SUMMARY OF THE INVENTION

The ventricular access device of this invention is a grommet in the form of a conduit with an extension extending outwardly from the conduit. The grommet is implanted in the myocardium of a ventricle. The grommet conduit penetrates the myocardium and provides an outlet for the flow of blood from the ventricle. The extension provides contact against the inner wall of the myocardium to retain the grommet in the myocardium notwithstanding the outward flow of blood from the ventricle. Preferably the grommet conduit is of sufficient length to allow a portion of said penetrating grommet conduit to be external to the ventricle when implanted in the myocardium. An external connector in the form of a conduit having an end adapted to connect to the external portion of the grommet conduit can be used to connect the grommet conduit to a primary external conduit.

The ventricular access device preferably further includes an introducer in the form of an elongated rod. The grommet is adapted to be mounted on the introducer for introduction into a ventricle and for penetration by the grommet conduit through the myocardium of the ventricle in an inside to outside manner.

The method of this invention is a surgical procedure for establishing an outlet for the flow of blood from a heart ventricle. In accordance with this method a grommet is introduced into the ventricle. The grommet is a conduit which provides an outlet in the ventricle wall (myocardium) for the egress of blood from the ventricle. The introduction of the grommet into the ventricle is preferably accomplished through the atrium and the atrioventricular valve. In the alternative, the grommet can be introduced through the ventricle wall. The grommet conduit is then caused to penetrate through the ventricle's myocardium in an inside to outside manner such that a portion of the grommet conduit is external to the ventricle. The grommet conduit is connected to a primary external conduit which is external to the ventricle. Preferably, the grommet conduit is connected to the primary external conduit by an external connector which engages the portion of the grommet conduit external to the ventricle. The grommet conduit is and remains positioned in the myocardium to provide an outlet through which blood from the ventricle can flow outwardly to the primary external conduit. Typically, the primary external conduit will be connected to the discending aorta, pulmonary artery, artificial heart assist device or other organ or device.

An introducer in the form of an elongated rod can be used to introduce the grommet into the ventricle and to cause the grommet conduit to penetrate the myocardium. Preferably the introducer includes a seat (extension) and a cone-shaped tip. The introducer is withdrawn after the grommet conduit is positioned in the myocardium.

Preferably the grommet includes an extension extending outwardly from the grommet conduit. The extension is brought into contact against the inner wall of the myocardium when the grommet conduit penetrates the myocardium. The extension functions to retain the grommet in the myocardium notwithstanding the outward flow of blood from the ventricle.

DETAILED DESCRIPTION OF THE INVENTION

Figure 1:
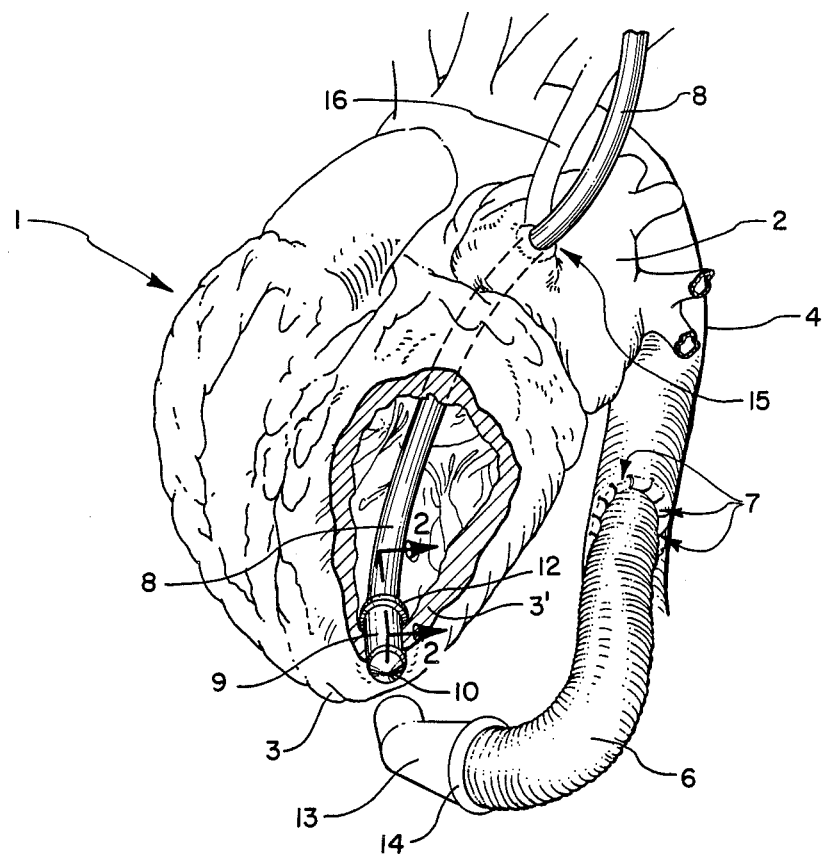
FIG. 1 depicts a human heart with the introducer in the left atrium and left ventricle and the grommet implanted in the myocardium of the left ventricle. Also depicted is an external connector and a primary external conduit attached to the descending aorta.
Figure 3:
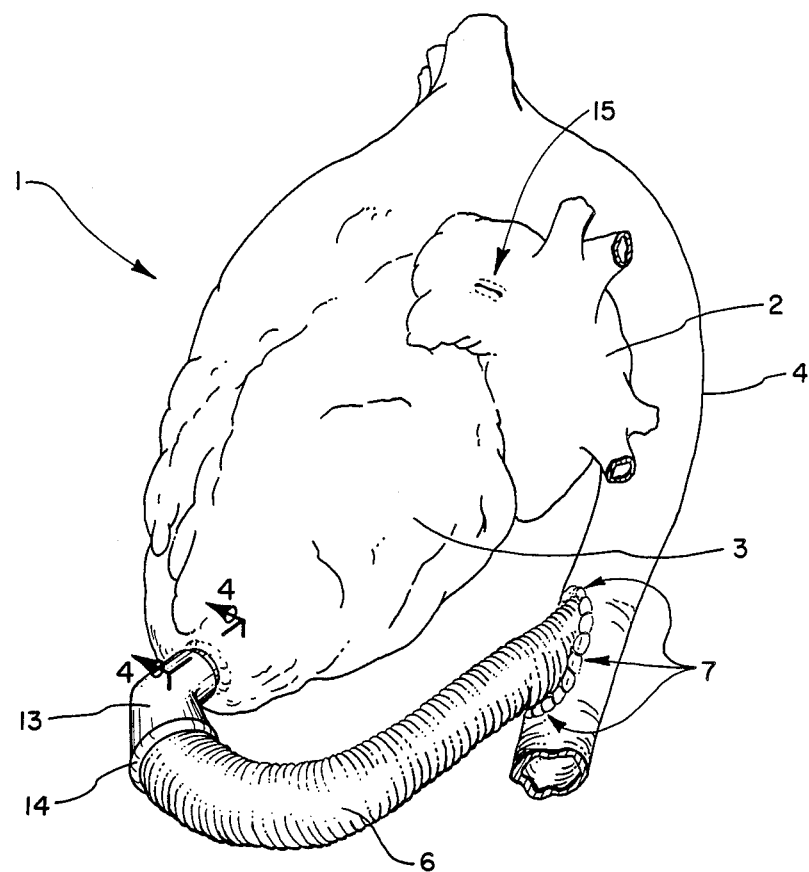
FIG. 3 depicts the external connector connecting the external portion of the grommet conduit to the primary external conduit which is attached to the descending aorta.

FIGS. 1 and 3 depict a human heart indicated generally by the numeral 1. The left atrium 2 of heart 1 is the chamber positioned above the left ventricle 3 (or lower chamber). The ventricle's myocardium (i.e. the endocardium, myocardium and epicardium collectively) is designated by the numeral 3' (see FIG. 1). The descending aorta 4 is also shown in both figures. The invention provides a surgical method and means for establishing an unobstructed outlet and path for blood flow from the left ventricle 3 to the descending aorta 4. The procedure can be accomplished without the need for use of myocardial sutures or cardiopulmonary bypass.

Figure 2:
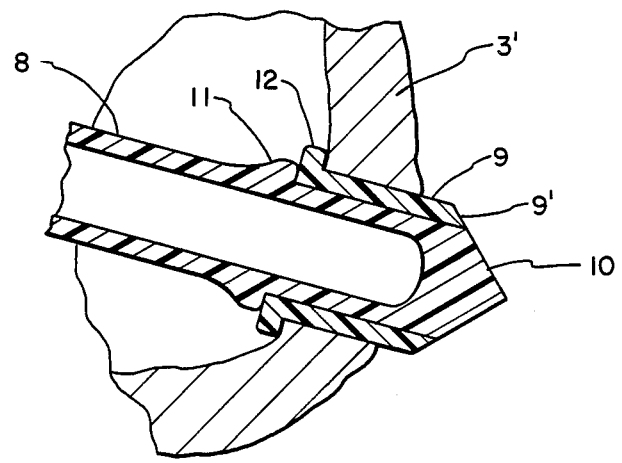
FIG. 2 depicts the leading end of the introducer and the grommet positioned in the myocardium.
Figure 4:
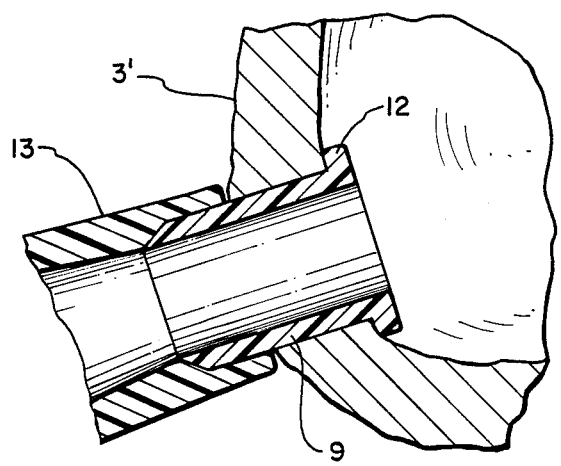
FIG. 4 depicts the grommet positioned in the myocardium with the introducer withdrawn. Also depicted is the friction fit between the external portion of the grommet conduit and the external connector.

FIGS. 1, 2 and 4 depict a grommet 9. The grommet 9 is a conduit which provides an outlet for the flow of blood from the ventricle 3 through the myocardium 3'. The grommet conduit 9 is cylindrical in shape and has a circular cross-section preferably of about 8 to 20 mm in diameter (I.D.). Although not preferred, other grommet conduit shapes are within the scope of this invention (e.g. a grommet conduit with a rectangular cross-section). The grommet 9 further includes an extension 12 extending outwardly from the grommet conduit. In this embodiment the extension 12 is a flange which extends around the body of the grommet conduit. The extension can be in forms other than a flange and can be integral with the grommet conduit or attached to it. Preferably, the flange 12 extends outwardly about 1½ to 4 mm from the surface of the grommet conduit 9. The flange 12 provides a surface for contact against the inner wall of the myocardium 3'. The grommet conduit 9 is sufficient in length from flange 12 (or other extension) to allow a portion of the grommet conduit to be external to the myocardium 3' and to allow for connection to external connector 13. Typically the length of the grommet conduit 9 will be about 8 to 18 mm. An important factor in determining any of the foregoing grommet dimensions is the thickness of a particular patient's myocardium 3'. In this embodiment the grommet 9 (including flange 12) is made of an integral piece of plastic. Any suitable plastic or other suitable material compatible with the human body can be used.

The introducer 8 is an elongated stainless steel rod preformed in shape to facilitate introduction and penetration of grommet conduit 9 through the myocardium 3'. The rod may be made of materials other than stainless steel (e.g. hard plastic). Preferably the rod has a circular cross-section. The diameter (or other cross-sectional dimension) of the introducer must allow for mounting of the grommet 9. A seat 11 extends outwardly from the introducer 8. The location of seat 11 allows for sufficient space on the introducer 8 to mount the grommet 9. The seat 11 can be an extension integral with or attached to the introducer 8. Preferably the leading end of the introducer 8 is a cone-shaped tip 10 which facilitates penetration of the myocardium 3'. Preferably the leading end of the grommet conduit 9 is behind the cone-shaped tip 10 (as illustrated in FIG. 2) and is beveled to form a bevel 9' (see FIG. 2) which serves to extend the cone-shaped tip 10 and to facilitate penetration of the myocardium 3'.

The grommet 9 is mounted on the introducer 8 by inserting the introducer into the grommet conduit and by positioning the grommet flange 12 against or near seat 11 as shown best in FIG. 2. The mounted grommet 9 is introduced through the left atrium 2 into left ventricle 3 as shown best in FIG. 1. Once inside the ventricle 3 the introducer 8 is used to cause the grommet conduit 9 to penetrate the myocardium 3'. This is accomplished by forcing the introducer and grommet conduit through the myocardium tissue. Removal of myocardium tissue by coring or otherwise is not required. This manner of myocardium penetration is referred to in this disclosure and the appended claims as "inside to outside" because the grommet 9 is first positioned inside of the ventricle and penetration proceeds from the inside of the ventricle to the outside of the ventricle. This is in contrast to the prior art procedure where coring of the myocardium and insertion of the stint proceed from the outside of the ventricle.

The introducer 8 and grommet conduit 9 are pushed through the myocardium 3' until the flange 12 contacts the inner wall of the myocardium 3' (see FIG. 2). A portion of the grommet conduit 9 extends beyond the outer wall of the myocardium 3', i.e. the portion is external to the ventricle 3. An external connector 13, in the form of a conduit, connects to the external portion of grommet conduit 9 (see FIGS. 3 and 4). In this embodiment external connector 13 is a female connector and grommet conduit 9 is a male connector and the female connector is placed over the external portion of the male connector to establish a friction fit between external connector 13 and grommet conduit 9. In this embodiment a friction fit is established but any other workable means of engaging, attaching, snapping together or otherwise connecting the external grommet conduit and external connector can be used. In an alternative embodiment within the scope of this invention as claimed, the primary external conduit 6 includes a means for direct connection to the external grommet conduit without the use of a separate external connector. In such an alternative embodiment the external connector is part of and integral with the primary external conduit 6 (i.e. an end of the primary external conduit serves as the external connector).

Following the connection of external connector 13 to grommet conduit 9, the introducer 8 is withdrawn leaving the grommet conduit 9 in place in the myocardium 3'. The external connector 13 functions to connect the grommet conduit 9 to primary external conduit 6. Primary external conduit 6 is attached to descending aorta 4. External connector 13 is angled to better accommodate primary external conduit 6. External connector 13 is made of a rigid plastic material (or other suitable material). Primary conduit 6 is made of a flexible dacron material (or other suitable material).

Blood flows from the ventricle 3 through grommet conduit 9, external connector 13 and primary external conduit 6 to the descending aorta 4. A conventional valve 14 allows for the flow of blood from ventricle 3 to the descending aorta 4 but prevents the flow of blood in the reverse direction, i.e. towards ventricle 3. The extension 12 functions to hold the grommet conduit 9 in place in the myocardium, i.e. contact of extension 12 against myocardium 3' prevents the outward flow of blood from the ventricle from pushing the grommet 9 out of the myocardium 3'. Thus, sutures are not needed in order to secure the grommet 9 in place and, therefore, an additional area of the myocardium need not be immobilized (as in the prior art procedure). Muscle contraction and the formation of myocardium scar tissue around the grommet conduit 9 further reinforce against displacement of the grommet from its position in the myocardium.

The scope of the invention is not limited to the embodiment depicted in FIGS. 1, 2, 3 and 4 and described above. Other variations including, but not limited to, the following examples, are within the scope of this invention. Introduction of the grommet into the left ventricle can be through the right atrium. The grommet implanted in the left ventricle can be used to allow for flow of blood from the left ventricle to the pulmonary artery or to an artificial device (e.g. left ventricular assist device LVAD). The grommet can be implanted in the right ventricle for allowing egress of blood to the pulmonary artery, descending aorta or artificial device. The invention is applicable to any situation where a ventricle outlet for the flow of blood from the ventricle needs to be established. It should be noted that the ventricular access device of this invention does not necessarily have to be implanted into the myocardium in an inside to outside manner pursuant to the inventive method. For example, the prior art outside to inside method can be used to implant the inventive device if the extension of the grommet conduit is retractable (i.e. the extension is extended outwardly from the conduit after the extension is positioned within the ventricle).

DESCRIPTION OF SURGICAL PROCEDURE

With reference to FIGS. 1, 2, 3 and 4 an example of the method of this invention is described below.

The surgical procedure begins with a thoracotomy (i.e. a surgical incision of the chest) on the side of the chest where the descending aorta 4 is located. The incision can be extended to the opposite side of the chest if additional exposure is needed. The purpose of the thoracotomy is to expose the heart and the great vessel (i.e. aorta or pulmonary artery). In this example, exposure of the descending aorta is desired. The pericardium anterior is incised and the edges retracted for exposure. The pericardium anterior is selected for the incision so as to avoid cutting the phrenic nerves. An incision is made on, and a purse string suture is placed about, a portion of the atrial appendage wall of left atrium 2 at the location designated by the number 15. Other locations on the left atrium 2 or the ventricle 3 could be selected in the alternative but are not preferred. Next, the descending aorta 4 is exposed by dissecting away tissue.

Prior to attachment to descending aorta 4 and left ventricle 3, primary external conduit 6 is soaked in a 25% albumin solution (or other clotting solution) and then autoclaved to reduce porosity. The conduit 6 can be, for example, a commercially available dacron conduit. The conduit 6 is cut to an appropriate length to fit comfortably between the left ventricle 3 and the descending aorta 4.

The patient is heparinized (i.e. a substance is injected into the blood to prevent clotting). A vascular clamp is placed on the descending aorta to block the flow of blood. The descending aorta 4 is then opened at location 7 and an end of conduit 6 is anastomosed (sutured) to the edges of the aorta opening at 7 (e.g. the conduit 6 can be sewn to the aorta 4 in an end-to-side fashion with a running suture technique). The suture line is tested to ensure a satisfactory suture. The vascular clamp is removed but not until after a second clamp is placed on primary external conduit 6 to prevent loss of blood from the aorta 4 through conduit 6. As an optional next step the left ventricle 3 is elevated on sponges.

The introducer 8 and mounted grommet 9 are inserted through the incision at location 15 and into the left atrium 2. The introducer 8 is shaped to facilitate introduction of the grommet 9. A rubber instrument 16 is used to hold the tissue tight against the introducer to reduce bleeding.

The introducer 8 carries the grommet 9 through the atrioventricular valve and into the left ventricle 3. The exact area of the myocardium 3' to be penetrated is identified. The cone-shaped tip 10 and grommet conduit 9 penetrate through the myocardium 3' at the identified area. The beveled portion 9' of the grommet conduit facilitates the penetration. The penetration causes minimal damage to the myocardium and no immobilizing myocardial sutures are used.

The second clamp is removed from primary external conduit 6 to allow the conduit to fill with blood and to deair. Valve 14 restricts loss of blood from primary external conduit 6 to a minimum.

When the penetrating grommet conduit 9 and introducer 8 have penetrated through the myocardium 3' and their external portions are visualized, the external connector 13 is connected to the grommet conduit 9. Following the connection of grommet conduit 9 to external connector 13 the introducer 8 is withdrawn leaving the grommet 9 in place in the myocardium 3'. The atrial purse string is tried down. Blood flow from the ventricle 3 through grommet conduit 9, external connector 13 and primary external conduit 6 to descending aorta 4 is established. Hemostasis (stoppage of bleeding) is obtained and chest tubes are inserted and connected to suction. The chest is then closed in a routine fashion and the procedure completed.

Because the invention is adaptable to a variety of congenital and acquired heart diseases and problems, the procedure will vary in actual practice. For example, the procedure will be different for each of the following: hypoplastic left heart syndrome (HLH), subaortic stenosis, aortic atresia and artificial heart assist devices. One difference in an HLH procedure, for example, would be the additional steps of encircling the pulmonary artery with premeasured tape and looping the patent ductus arteriosus and subsequently banding the pulmonary artery (by tightening the tape to narrow the artery) to restrict blood flow and ligating the looped ductus. Because these differences are well within the scope of the knowledge and expertise of persons of ordinary skill in the relevant art and because such differences do not relate to the essence of this invention, detailed discussion thereof is not provided in this disclosure.

The foregoing description of a specific embodiment of this invention so fully reveals the general nature of the invention that others can, by applying current knowledge, readily modify such specific embodiment and/or adapt it for various applications without departing from the generic concept, and, therefore, such adaptations and modifications should and are intended to be comprehended within the meaning and range of equivalents of the following claims, which claims define subject matter regarded to be our invention.

We claim:

1. A ventricular access device for establishing and allowing egress of blood from a heart ventricle comprising:
   (a) an introducer comprising an elongated rod,
   (b) a grommet comprising a conduit and an extension extending outwardly from said conduit; wherein said grommet is sized and shaped to be mounted on said introducer;
wherein said introducer is adapted to introduce said grommet, when mounted on said introducer, into said ventricle and to cause said grommet conduit to penetrate the myocardium of said ventricle in an inside to outside manner such that a portion of said grommet conduit is external to said ventricle; wherein said grommet conduit is adapted to provide an outlet for the flow of blood from said ventricle; and wherein said extension is adapted to provide contact against the inner wall of said myocardium to retain said grommet in said myocardium notwithstanding the outward flow of blood from said ventricle.

2. A device in accordance with claim 1 wherein the leading end of said introducer is a cone-shaped tip to facilitate the penetration of said myocardium and wherein the leading end of said grommet conduit is behind said cone-shaped tip.

3. A device in accordance with claim 2 wherein the leading end of said grommet conduit is beveled to extend said cone-shaped tip.

4. A device in accordance with claim 1 wherein said introducer further comprises a seat extending from said introducer at a location behind the position occupied by said grommet when mounted on said introducer; and wherein said seat functions to prevent said grommet from being pushed back along said introducer during introduction into said ventricle and penetration of said ventricle's myocardium.

5. A device in accordance with claim 1 further comprising (c) an external connector; wherein said external connector is comprised of a conduit having an end adapted to connect to the external portion of said grommet conduit.

6. A surgical method for establishing an outlet for the flow of blood from a heart ventricle comprising:
   (a) introducing a grommet into said ventricle; wherein said grommet comprises a conduit,
   (b) causing said grommet conduit to penetrate through the myocardium of said ventricle in an inside to outside manner such that a portion of said grommet conduit is external to said ventricle, and
   (c) connecting said grommet conduit to a primary external conduit which is external to said ventricle;
wherein said grommet conduit is and remains positioned in said myocardium to provide an outlet through which blood from said ventricle can flow outwardly to said primary external conduit.

7. A surgical method in accordance with claim 6, further comprising:
   (d) connecting said primary external conduit to a member selected from the group consisting of descending aorta, pulmonary artery and artificial heart assist device;
wherein the order in which step (d) is performed is independent of the order in which steps (a), (b) and (c) are performed.

8. A surgical method in accordance with claim 6 wherein said grommet is mounted on an introducer; wherein said introducer is comprised of an elongated rod; wherein said introducer is used to introduce said grommet into said ventricle and to cause said grommet conduit to penetrate said myocardium; and wherein said introducer is withdrawn from said ventricle after said grommet conduit is positioned in said myocardium.

9. A surgical method in accordance with claim 8 wherein the leading end of said introducer is a cone-shaped tip to facilitate the penetration of said myocardium.

10. A surgical method in accordance with claim 8 wherein said introducer further comprises a seat extending outwardly from said introducer at a location behind the position occupied by the mounted grommet; and wherein said seat functions to prevent said grommet from being pushed back along said introducer during steps (a) and (b).

11. A surgical method in accordance with claim 6 wherein said grommet includes an extension extending from said grommet conduit which extension is brought into contact against the inner wall of said myocardium when the grommet conduit penetrates said myocardium; and wherein said extension functions to retain said grommet in said myocardium notwithstanding the outward flow of blood from said ventricle.

12. A surgical method in accordance with claim 11 wherein said extension is a flange.

13. A surgical method in accordance with claim 6 wherein said grommet conduit is connected to said primary external conduit by an external connector; wherein said external connector is comprised of a conduit; and wherein said external connector engages the portion of said grommet conduit external to said ventricle.

14. A surgical method in accordance with claim 13 wherein said external connector is a female connector and said grommet conduit is a male connector; and wherein said female connector is placed over said external grommet conduit portion to establish a friction fit between said external connector and said grommet conduit.

15. A surgical method in accordance with claim 13 wherein said external connector is angled.

16. A surgical method in accordance with claim 6 wherein said grommet is introduced through an atrium and an atrioventricular valve into said ventricle.

17. A surgical method in accordance with claim 6 wherein said grommet under step (a) is introduced through the ventricle wall into said ventricle.

* * * * *